(12) United States Patent
Michael

(10) Patent No.: US 9,245,405 B2
(45) Date of Patent: *Jan. 26, 2016

(54) CABINET SYSTEM

(71) Applicant: AutoMed Technologies, Inc., Buffalo Grove, IL (US)

(72) Inventor: James A. Michael, Cranberry Township, PA (US)

(73) Assignee: AutoMed Technologies, Inc., Buffalo Grove, IL (US)

( * ) Notice: Subject to any disclaimer, the term of this patent is extended or adjusted under 35 U.S.C. 154(b) by 135 days.

This patent is subject to a terminal disclaimer.

(21) Appl. No.: 14/054,480

(22) Filed: Oct. 15, 2013

(65) Prior Publication Data

US 2014/0046482 A1    Feb. 13, 2014

Related U.S. Application Data

(63) Continuation of application No. 13/032,753, filed on Feb. 23, 2011, now Pat. No. 8,588,966, which is a continuation-in-part of application No. 12/351,679, filed on Jan. 9, 2009, now Pat. No. 8,103,379.

(51) Int. Cl.
*G06F 17/00* (2006.01)
*G07F 11/18* (2006.01)
(Continued)

(52) U.S. Cl.
CPC ............... *G07F 11/18* (2013.01); *A61J 7/0084* (2013.01); *E05B 47/00* (2013.01); *E05B 65/462* (2013.01);
(Continued)

(58) Field of Classification Search
CPC ........ A61J 7/0084; G07F 11/18; G07F 11/60; G07F 11/62; G07F 17/0092
USPC ................... 221/122, 133; 700/236, 242, 243
See application file for complete search history.

(56) References Cited

U.S. PATENT DOCUMENTS 2,246,626 A    6/1941 Grandin
2,412,332 A   12/1946 Hansen
(Continued)

FOREIGN PATENT DOCUMENTS

EP    0488548 A1    6/1992
JP    2001-275766    10/2001
(Continued)

OTHER PUBLICATIONS

European Search Report and Written Opinion for European Patent application No. 09838015.7, dated Jan. 26, 2015. 6 pages.
(Continued)

*Primary Examiner* — Timothy Waggoner
(74) *Attorney, Agent, or Firm* — Reinhart Boerner Van Deuren s.c.

(57) ABSTRACT

A cabinet system for securely storing items includes a cabinet housing, a controller, and at least one drawer unit. The cabinet housing has a locking mechanism, and the controller is in communication with the cabinet housing and configured to operate the locking mechanism. The drawer unit is designed to be releasably locked at least partially within the cabinet housing by the locking mechanism, and slidable within a portion of the cabinet housing when released by the locking mechanism. The drawer unit includes at least one storage compartment, a cover, memory, and a power source. The storage compartment is configured to store at least one item therein. The cover is movable to an open configuration and a closed configuration. When the cover is in the closed configuration, the cover limits access to the item of the storage compartment. The memory is powered by the power source and is configured to store data associated with a movement of the cover.

20 Claims, 7 Drawing Sheets

(51) Int. Cl.
*A61J 7/00* (2006.01)
*E05B 47/00* (2006.01)
*E05B 65/46* (2006.01)
*G07F 11/60* (2006.01)
*G07F 11/62* (2006.01)
*G07F 17/00* (2006.01)
*H04Q 9/00* (2006.01)

(52) U.S. Cl.
CPC ............... *G07F 11/60* (2013.01); *G07F 11/62* (2013.01); *G07F 17/0092* (2013.01); *H04Q 9/00* (2013.01); *E05B 2047/0094* (2013.01); *H04Q 2209/30* (2013.01); *H04Q 2209/823* (2013.01)

(56) References Cited

U.S. PATENT DOCUMENTS

| | | | |
|---|---|---|---|
| 3,154,880 A | 11/1964 | Campbell | |
| 3,286,390 A | 11/1966 | Guice | |
| 3,682,113 A | 8/1972 | McClellan et al. | |
| 4,057,145 A | 11/1977 | Wray et al. | |
| 4,267,942 A | 5/1981 | Wick, Jr. et al. | |
| 4,351,435 A | 9/1982 | Elwert et al. | |
| 4,785,969 A | 11/1988 | McLaughlin | |
| 4,865,404 A | 9/1989 | Harper | |
| 4,927,051 A | 5/1990 | Falk et al. | |
| 4,941,570 A | 7/1990 | Kruger et al. | |
| 5,014,875 A | 5/1991 | McLaughlin et al. | |
| 5,046,455 A | 9/1991 | Christiansen et al. | |
| 5,087,107 A | 2/1992 | Fumanelli | |
| 5,222,789 A | 6/1993 | Yoshikawa | |
| 5,246,136 A | 9/1993 | Loidl | |
| 5,255,971 A | 10/1993 | Aisley | |
| 5,259,668 A | 11/1993 | Teufel et al. | |
| 5,263,596 A | 11/1993 | Williams | |
| 5,282,678 A | 2/1994 | Teufel et al. | |
| 5,322,365 A | 6/1994 | Teufel et al. | |
| 5,346,297 A | 9/1994 | Colson, Jr. et al. | |
| 5,377,864 A | 1/1995 | Blechl et al. | |
| 5,404,384 A | 4/1995 | Colburn et al. | |
| 5,405,048 A | 4/1995 | Rogers et al. | |
| 5,445,295 A | 8/1995 | Brown | |
| 5,460,294 A | 10/1995 | Williams | |
| 5,520,450 A | 5/1996 | Colson, Jr. et al. | |
| 5,533,079 A | 7/1996 | Colburn et al. | |
| 5,713,485 A | 2/1998 | Liff et al. | |
| 5,724,764 A | 3/1998 | Alsup | |
| 5,743,607 A | 4/1998 | Teufel et al. | |
| 5,745,366 A | 4/1998 | Higham et al. | |
| 5,790,409 A | 8/1998 | Fedor et al. | |
| 5,797,515 A | 8/1998 | Liff et al. | |
| 5,805,456 A | 9/1998 | Higham et al. | |
| 5,839,257 A | 11/1998 | Soderstrom et al. | |
| 5,848,593 A | 12/1998 | McGrady et al. | |
| 5,905,653 A | 5/1999 | Higham et al. | |
| 5,912,818 A | 6/1999 | McGrady et al. | |
| 5,927,540 A | 7/1999 | Godlewski | |
| 5,961,036 A | 10/1999 | Michael et al. | |
| 6,011,999 A | 1/2000 | Holmes | |
| 6,019,249 A | 2/2000 | Michael et al. | |
| 6,068,156 A | 5/2000 | Liff et al. | |
| 6,073,834 A | 6/2000 | Michael et al. | |
| 6,109,774 A | 8/2000 | Holmes et al. | |
| 6,116,461 A * | 9/2000 | Broadfield et al. | 221/98 |
| 6,151,536 A | 11/2000 | Arnold et al. | |
| 6,163,737 A | 12/2000 | Fedor et al. | |
| 6,170,230 B1 | 1/2001 | Chudy et al. | |
| 6,170,929 B1 | 1/2001 | Wilson et al. | |
| 6,175,779 B1 | 1/2001 | Barrett | |
| 6,256,967 B1 | 7/2001 | Hebron et al. | |
| 6,338,007 B1 | 1/2002 | Broadfield et al. | |
| 6,401,991 B1 | 6/2002 | Eannone | |
| 6,427,865 B1 | 8/2002 | Stillwell et al. | |
| 6,471,089 B2 | 10/2002 | Liff et al. | |
| 6,502,718 B2 | 1/2003 | Fitzgerald et al. | |
| 6,564,121 B1 | 5/2003 | Wallace et al. | |
| 6,581,798 B2 | 6/2003 | Liff et al. | |
| 6,594,549 B2 | 7/2003 | Siegel | |
| 6,609,047 B1 | 8/2003 | Lipps | |
| 6,625,952 B1 | 9/2003 | Chudy et al. | |
| 6,650,964 B2 | 11/2003 | Spano, Jr. et al. | |
| 6,658,322 B1 | 12/2003 | Frederick et al. | |
| 6,662,081 B1 | 12/2003 | Jacober et al. | |
| 6,735,497 B2 | 5/2004 | Wallace et al. | |
| 6,742,671 B2 | 6/2004 | Hebron et al. | |
| 6,746,091 B2 | 6/2004 | Friar et al. | |
| 6,760,643 B2 | 7/2004 | Lipps | |
| 6,775,591 B1 | 8/2004 | Shoenfeld | |
| 6,776,304 B2 | 8/2004 | Bossi et al. | |
| 6,776,306 B1 | 8/2004 | Michael et al. | |
| 6,785,589 B2 | 8/2004 | Eggenberger et al. | |
| 6,788,997 B1 | 9/2004 | Frederick | |
| 6,814,254 B2 | 11/2004 | Liff et al. | |
| 6,814,255 B2 | 11/2004 | Liff et al. | |
| 6,847,861 B2 | 1/2005 | Lunak et al. | |
| 6,895,304 B2 | 5/2005 | Spano, Jr. et al. | |
| 6,902,083 B1 | 6/2005 | Michael et al. | |
| 6,916,447 B2 | 7/2005 | Kowallis | |
| 6,963,791 B1 | 11/2005 | Frederick et al. | |
| 6,975,922 B2 | 12/2005 | Duncan et al. | |
| 6,985,797 B2 | 1/2006 | Spano, Jr. et al. | |
| 6,996,455 B2 | 2/2006 | Eggenberger et al. | |
| 6,997,377 B2 | 2/2006 | Washington et al. | |
| 7,006,893 B2 | 2/2006 | Hart et al. | |
| 7,010,389 B2 | 3/2006 | Lanak et al. | |
| 7,040,504 B2 | 5/2006 | Broadfield et al. | |
| 7,044,569 B1 | 5/2006 | Relyea et al. | |
| 7,048,142 B2 | 5/2006 | Michael et al. | |
| 7,052,097 B2 | 5/2006 | Meek, Jr. et al. | |
| 7,072,737 B2 | 7/2006 | Lunak et al. | |
| 7,077,286 B2 | 7/2006 | Shows et al. | |
| 7,080,755 B2 * | 7/2006 | Handfield et al. | 221/13 |
| 7,151,982 B2 | 12/2006 | Liff et al. | |
| 7,152,441 B2 | 12/2006 | Friar et al. | |
| 7,228,200 B2 | 6/2007 | Baker et al. | |
| 7,258,241 B2 | 8/2007 | Reid | |
| 7,258,249 B1 | 8/2007 | Frederick et al. | |
| 7,262,698 B1 | 8/2007 | Frederick et al. | |
| 7,263,410 B1 | 8/2007 | Frederick et al. | |
| 7,286,900 B1 | 10/2007 | Frederick et al. | |
| 7,293,672 B2 | 11/2007 | Mori et al. | |
| 7,293,673 B2 | 11/2007 | Savage et al. | |
| 7,349,858 B1 | 3/2008 | McGrady et al. | |
| 7,395,945 B2 | 7/2008 | Godlewski | |
| 7,426,425 B2 | 9/2008 | Meek, Jr. et al. | |
| 7,427,002 B2 | 9/2008 | Liff et al. | |
| 7,427,022 B2 | 9/2008 | Yokota et al. | |
| 7,434,704 B2 | 10/2008 | Yuyama et al. | |
| 7,463,947 B1 | 12/2008 | Frederick et al. | |
| 7,464,832 B2 | 12/2008 | Lee | |
| 7,467,093 B1 | 12/2008 | Newton et al. | |
| 7,502,666 B2 | 3/2009 | Siegel et al. | |
| 7,515,988 B1 | 4/2009 | Frederick et al. | |
| 7,596,427 B1 | 9/2009 | Frederick et al. | |
| 7,630,789 B2 | 12/2009 | Broadfield et al. | |
| 7,630,791 B2 | 12/2009 | Nguyen et al. | |
| 7,637,374 B2 | 12/2009 | Fried | |
| 7,685,026 B1 | 3/2010 | McGrady et al. | |
| 7,689,316 B1 | 3/2010 | Frederick et al. | |
| 7,689,317 B2 | 3/2010 | McGrady et al. | |
| 7,719,420 B2 | 5/2010 | Christie et al. | |
| 7,726,095 B2 | 6/2010 | Yuyama et al. | |
| 7,751,932 B1 | 7/2010 | Fedor et al. | |
| 7,805,216 B2 | 9/2010 | Shows et al. | |
| 7,823,993 B2 | 11/2010 | Ostrowski | |
| 7,848,846 B2 | 12/2010 | Uema et al. | |
| 7,991,507 B2 | 8/2011 | Liff et al. | |
| 8,068,932 B2 * | 11/2011 | Kirzinger | 700/237 |
| 8,096,628 B2 | 1/2012 | Ostrowski | |
| 8,103,379 B2 | 1/2012 | Biba et al. | |
| 8,197,017 B2 | 6/2012 | Rahilly | |
| 8,231,749 B2 | 7/2012 | Dent et al. | |
| 8,234,008 B2 | 7/2012 | Weber | |

(56) References Cited

U.S. PATENT DOCUMENTS

| | | |
|---|---|---|
| 8,588,966 B2 * | 11/2013 | Michael .................. 700/242 |
| 2001/0019065 A1 | 9/2001 | William et al. |
| 2001/0044731 A1 | 11/2001 | Coffman et al. |
| 2003/0088333 A1 | 5/2003 | Liff et al. |
| 2004/0026442 A1 | 2/2004 | Hutchinson |
| 2004/0104652 A1 | 6/2004 | Holmes et al. |
| 2004/0134043 A1 | 7/2004 | Uema et al. |
| 2004/0158350 A1 | 8/2004 | Ostergaard et al. |
| 2005/0145644 A1 | 7/2005 | Mori et al. |
| 2006/0079994 A1 | 4/2006 | Chu et al. |
| 2006/0125356 A1 | 6/2006 | Meek, Jr. et al. |
| 2006/0151517 A1 | 7/2006 | Varis |
| 2006/0197419 A1 | 9/2006 | Sorensen |
| 2006/0228131 A1 | 10/2006 | Kimura et al. |
| 2006/0277269 A1 | 12/2006 | Dent et al. |
| 2007/0023193 A1 | 2/2007 | King |
| 2007/0078562 A1 | 4/2007 | Park et al. |
| 2007/0208598 A1 | 9/2007 | McGrady et al. |
| 2007/0262147 A1 | 11/2007 | Braun et al. |
| 2007/0283733 A1 | 12/2007 | Ratkus et al. |
| 2008/0065264 A1 | 3/2008 | Omura et al. |
| 2008/0129171 A1 | 6/2008 | Greiner |
| 2008/0190953 A1 | 8/2008 | Mallett et al. |
| 2009/0015116 A1 | 1/2009 | Arceta et al. |
| 2009/0055018 A1 | 2/2009 | Meek, Jr. et al. |
| 2009/0108016 A1 | 4/2009 | Brown et al. |
| 2009/0114672 A1 | 5/2009 | Schifman et al. |
| 2009/0138122 A1 | 5/2009 | Wagner |
| 2010/0079240 A1 | 4/2010 | Higham |
| 2010/0176699 A1 | 7/2010 | Biba et al. |
| 2010/0228392 A1 | 9/2010 | Braun |
| 2011/0012374 A1 | 1/2011 | Ostrowski |
| 2011/0015782 A1 | 1/2011 | Chudy et al. |
| 2011/0101018 A1 | 5/2011 | Shafir |
| 2011/0140831 A1 | 6/2011 | Michael |
| 2011/0156560 A1 | 6/2011 | Michael |
| 2011/0196538 A1 | 8/2011 | Michael |
| 2011/0266929 A1 | 11/2011 | Michael |

FOREIGN PATENT DOCUMENTS

| | | |
|---|---|---|
| JP | 2003509084 | 3/2003 |
| JP | 2005143401 A | 6/2005 |
| JP | 2005287609 A | 10/2005 |
| JP | 2007126270 | 5/2007 |
| KR | 10/0963597 | 6/2010 |
| WO | WO 00/32073 | 6/2000 |
| WO | WO 2010-080660 | 7/2010 |

OTHER PUBLICATIONS

U.S. Appl. No. 09/086,857, filed May 29, 2998, Frederick et al.
International Search Report and Written Opinion for International Application No. PCT/US2012/025673, mail date Dec. 26, 2012, 10 pages.
International Search Report and Written Opinion for International Application No. PCT/US2012/030922, mailed on Oct. 18, 2012, 12 pages.
International Search Report and Written Opinion for International Application No. PCT/US12/026156, mail date Dec. 10, 2012, 9 pages.
International Search Report and Written Opinion for International Application No. PCT/US2009/069432, mail date Aug. 27, 2010, 6 pages.
English language translation of JP 2007126270 provided by foreign associate on Dec. 27, 2013, 13 pages.

* cited by examiner (1)

CABINET SYSTEM

CROSS-REFERENCE TO RELATED APPLICATIONS

This application is a continuation of U.S. application Ser. No. 13/032,753, filed Feb. 23, 2011, which is a continuation-in-part of U.S. application Ser. No. 12/351,679, filed Jan. 9, 2009, which are incorporated herein by reference in their entireties.

BACKGROUND

The present disclosure relates generally to the field of cabinetry for storing medical supplies, such as pharmaceuticals, medical devices and other health care related items. More specifically, the present disclosure relates to a cabinet system for providing security and monitoring related to stored items, such as medical supplies.

SUMMARY

An embodiment of the invention relates to a medical item storage cabinet system. They system includes a cabinet including a plurality of drawer bays and a data bus. Each bay slidably accepts a drawer and permits movement of the drawer between an open and closed position. The system further includes a plurality of drawers. Each drawer slides within a respective bay of the cabinet. The cabinet may include drawers which are all secured, or a combination of secured and unsecured drawers. The secured drawers each include at least one compartment secured closed by a cover movable between open and closed positions to permit access to the compartment. An electronic memory is attached to the drawer and stores movement data representative of movement of the cover. A cover monitoring device is coupled to the memory to permit the memory to store movement data representative of movement of the cover. A connector is attached to the drawer and coupled to the memory. The connector makes contact with the data bus when the drawer is in the closed position, and disconnects from the data bus when the drawer is in the open position. A locking mechanism selectively locks each drawer within its respective bay in a closed position. A controller is provided to control operation of the locking mechanism, and store data representative of the information stored in the electronic memory of a drawer.

Another embodiment of the invention relates to a cabinet system for securely storing items. The cabinet system includes a cabinet housing, a controller, and at least one drawer unit. The cabinet housing has a locking mechanism, and the controller is coupled to the cabinet housing and configured to operate the locking mechanism. The drawer unit is designed to be releasably locked at least partially within the cabinet housing by the locking mechanism, and slidable within a portion of the cabinet housing when released by the locking mechanism. The drawer unit includes at least one storage compartment, a cover, memory, and a power source. The storage compartment is configured to store at least one item therein. The cover is movable to an open configuration and a closed configuration, such that when the cover is in the closed configuration, the cover limits access to the item of the storage compartment. The memory is powered by the power source and is configured to store data associated with movement of the cover.

Another embodiment of the invention relates to a cabinet system for securely storing items. The cabinet system includes a cabinet housing, a controller, at least one drawer unit, and memory. The cabinet housing has a locking mechanism, and the controller is coupled to the cabinet housing and configured to operate the locking mechanism. The drawer unit is releasably locked at least partially within the cabinet housing by the locking mechanism, and slidable within a portion of the cabinet housing when released by the locking mechanism. The drawer unit includes at least one storage compartment and a belt. The storage compartment is configured to store at least one item therein, and the belt is slidable relative to the storage compartment, to an open configuration and a closed configuration. When the belt is in the closed configuration, the belt limits access to the item of the storage compartment. The memory is configured to store data representative of a movement of the belt.

Yet another embodiment of the invention relates to a cabinet system for securely storing items. The cabinet system includes a cabinet housing, at least one drawer unit, memory, a controller, and an alarm. The cabinet housing has a locking mechanism, and the drawer unit is configured to be releasably locked at least partially within the cabinet housing by the locking mechanism. The drawer unit is also configured to be slidable within a portion of the cabinet housing when released by the locking mechanism. The drawer unit includes at least one storage compartment and a cover. The storage compartment is configured to store at least one item therein. The cover is movable to an open configuration and a closed configuration, where the cover limits access to the item of the storage compartment when the cover is in the closed configuration. The memory is connected to the cover and designed to store data representative of a movement of the cover. The controller is in communication with the cabinet housing and configured to operate the locking mechanism, and to permit an authorized access to the item of the storage compartment. The alarm is configured to be triggered in response to the cover being moved without the controller having authorized access to the item of the storage compartment.

Alternative exemplary embodiments relate to other features and combinations of features as may be generally recited in the claims.

BRIEF DESCRIPTION OF THE FIGURES

The present invention will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the present invention is not limited to the details or methodology set forth in the description or illustrated in the figures. It should also be understood that the terminology is for the purpose of description only and should not be regarded as limiting.

Access to medical items, such as medications, medical instruments, medicinal applicators, healthcare-related articles, or other items, may be controlled by a storage cabinet system (e.g., medication cabinetry) designed to inhibit misuse, mistaken use, and theft of such items. The cabinet system may be used by doctors, nurses, technicians, pharmacists, and others to store and controllably distribute the items. In at least one embodiment disclosed herein, a cabinet system provides selective access to the items, which are stored in one or more drawer units of the cabinet system. The cabinet system is sensitive to unauthorized attempts to access the contents of the one or more drawer units, and stores data representative of such attempts, whether or not the attempts are successful.

Figure 1:
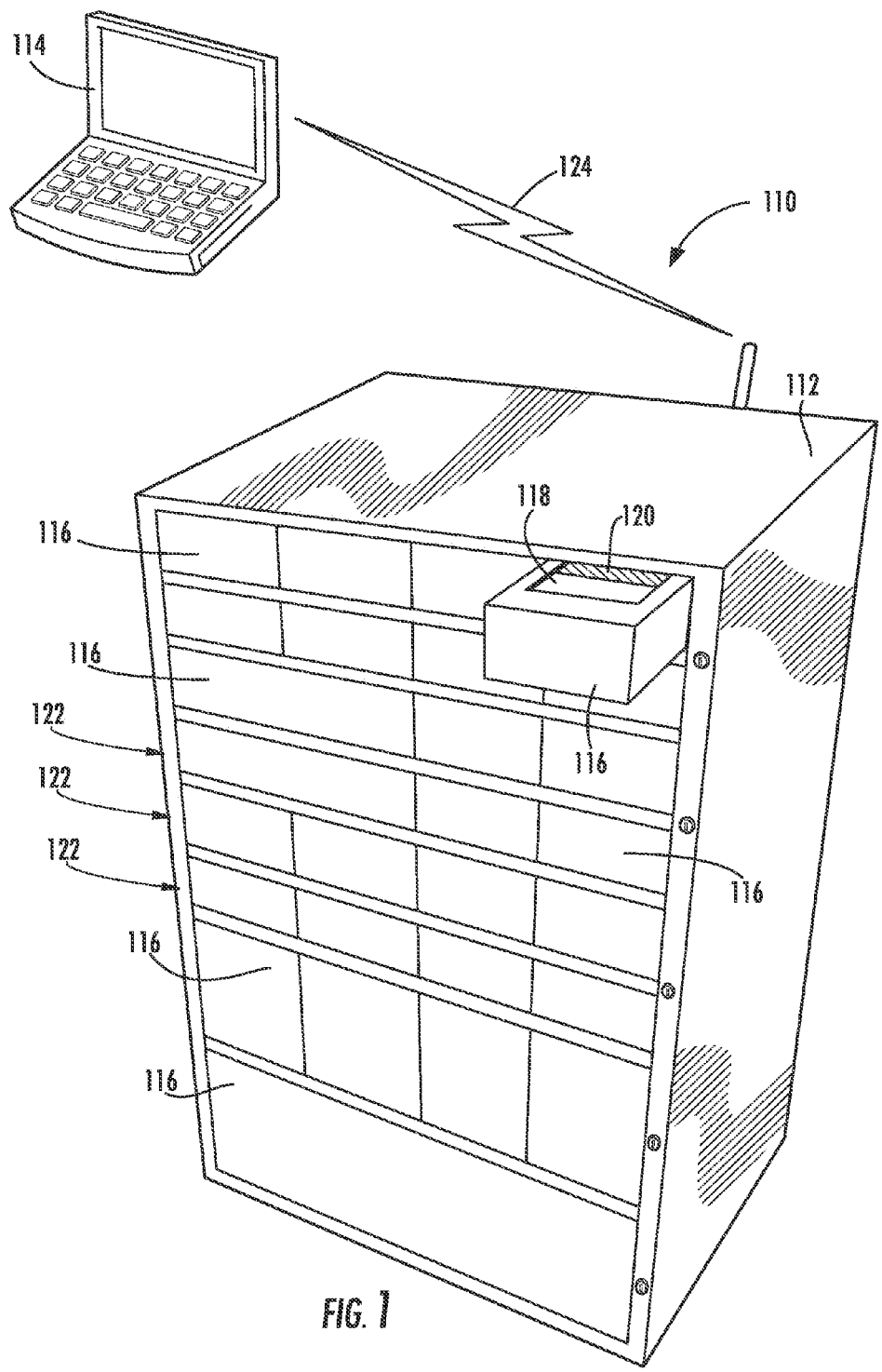
FIG. 1 is a perspective view of a cabinet system according to an exemplary embodiment of the invention.
Figure 3:
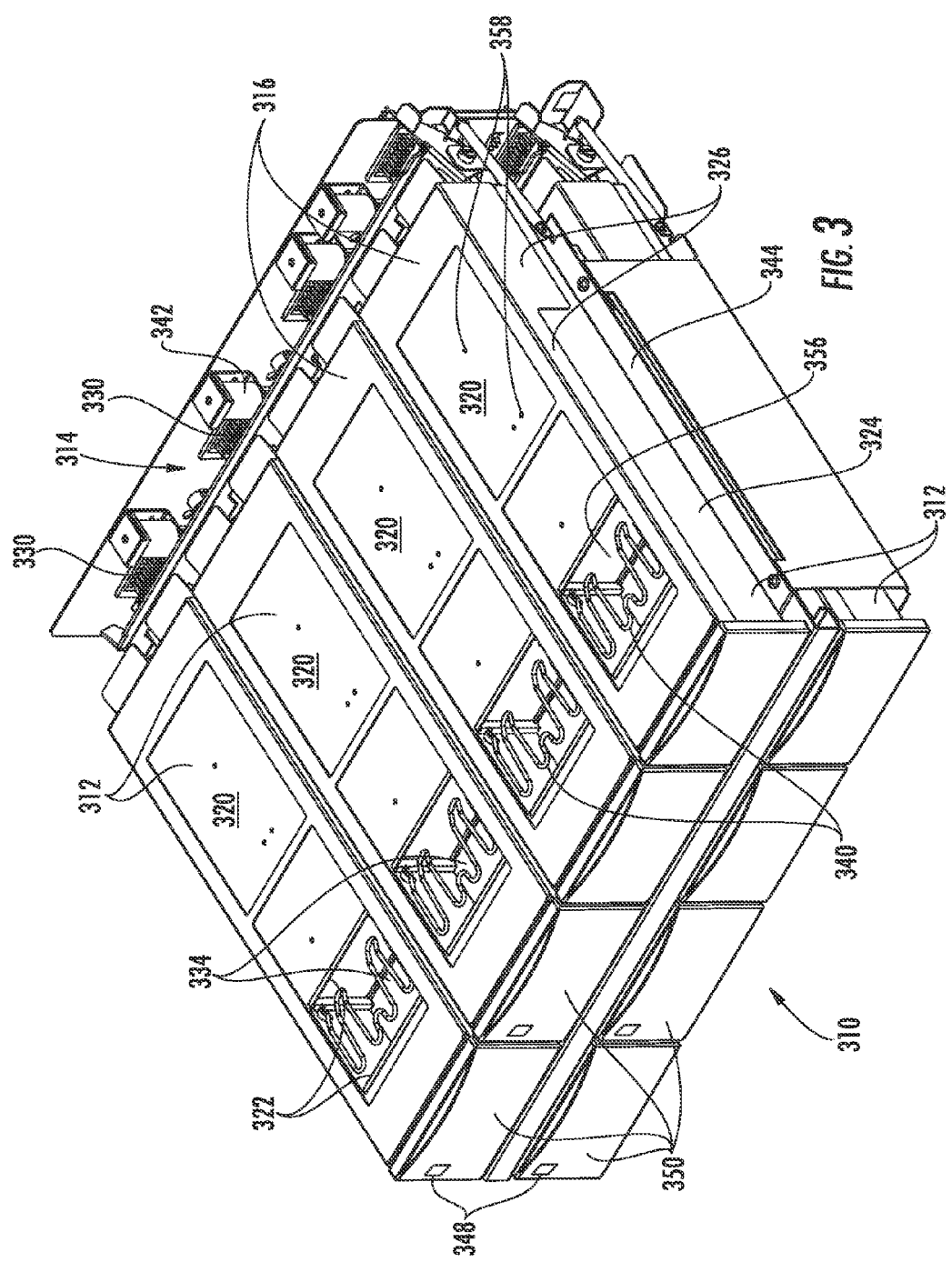
FIG. 3 is a perspective view of a portion of a cabinet system according to an exemplary embodiment of the invention.

Referring to FIG. 1, a cabinet system 110 (e.g., dispensing station) includes a cabinet housing 112 (e.g., frame), a controller 114, and one or more drawer units 116 (e.g., secure drawers with lids). According to an exemplary embodiment, the drawer units 116 of the cabinet system 110 are arranged in one or more vertically-stacked rows 122, each row 122 including one or more drawer units 116. The drawer units 116 of the rows 122 may be uniform in size (see, e.g., assembly 310 of drawer units 312 as shown in FIG. 3), or may include a variety of different sizes and relative capacities.

Figure 2:
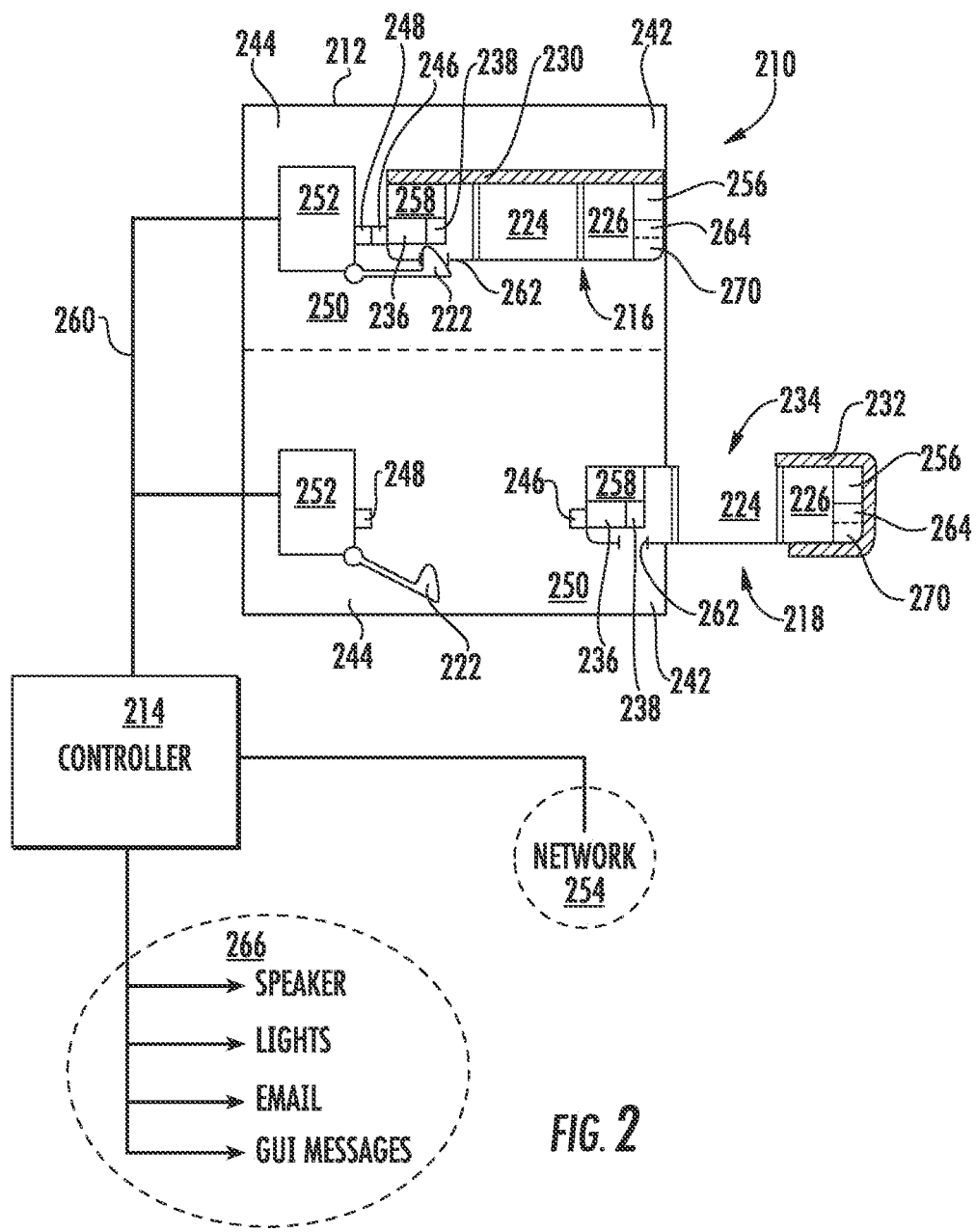
FIG. 2 is a schematic diagram of a cabinet system according to another exemplary embodiment of the invention.

One or more of the drawer units 116 are configured to be releasably locked at least partially within the cabinet housing 112 by a locking mechanism (see, e.g., locking mechanism 222 as shown in FIG. 2). Locking of the drawer unit 116 within the cabinet housing 112 may inhibit unauthorized access to contents of the drawer unit 116, and/or unauthorized removal of the entire drawer unit 116. However, when the locking mechanism is released, the drawer unit 116 may be slid relative to the cabinet housing 112, such as pulled partially or fully out of the cabinet housing 112.

Still referring to FIG. 1, each drawer unit 116 includes a storage compartment 118 (e.g., container) and a cover 120 coupled thereto. The storage compartment 118 is designed to securely store one or more items therein, such as medical supplies, and the cover 120 is designed to move to an open configuration and a closed configuration. While in a closed configuration, the cover 120 is designed to limit access to the items of the storage compartment 118. However, when the cover 120 is in the open configuration and the drawer unit 116 has been sufficiently slid from the cabinet housing 112, contents of the storage compartment 118 may be accessible for removal from the drawer unit 116.

In FIG. 1, the controller 114 is shown to include a computer terminal (e.g., laptop computer). The controller 114 is in communication (e.g., wireless communication 124 or over a wired network) with at least one of the cabinet housing 112 and/or one of the drawer units 116. According to an exemplary embodiment, the controller 114 is configured to control operation of the locking mechanism, so as to control the release of the locking mechanism and correspondingly release the drawer unit 116 with respect to the cabinet housing 112. In some embodiments, the controller 114 is further configured to control movement of the cover 120, such as to move the cover 120 from the closed configuration to the open configuration, and/or visa versa.

According to an exemplary embodiment, at least one of the drawer units 116 includes a tamper detection system. After the drawer unit 116 has been released from the locking mechanism and the cover 120 is in the open configuration relative to one of several compartments, the drawer unit 116 is sensitive to additional movements of the cover 120 or other covers associated with the drawer where individual covers are used in place of a single cover. For example, if a would-be thief attempts to manually force movement of the cover 120 to gain unauthorized access to additional compartments, a component(s) (e.g., sensor) of the drawer unit 116 provides notice of the attempt—regardless of whether the attempt was successful or not. In some embodiments, the component generates a signal that triggers an alarm. In some embodiments, the signal is stored in memory coupled to the drawer unit 116, and/or communicated to the controller 114 to be analyzed and possibly further communicated. In other contemplated embodiments, the memory may be coupled to the cabinet housing 112 or to the controller 114.

Referring now to FIG. 2, a cabinet system 210 includes a cabinet housing 212, a controller 214, and drawer units 216, 218. According to an exemplary embodiment, each drawer unit 216, 218 includes at least a first storage compartment 224 and a second storage compartment 226. Each storage compartment 224, 226 is configured to store (e.g., hold, contain) one or more items. A locking mechanism 222 is configured to releasably lock each drawer unit 216, 218 at least partially within the cabinet housing 212—for example, substantially within the cabinet housing 212, but with an end (e.g., face, handle, extensions) of each drawer unit 216, 218 extending from the cabinet housing 212.

As shown in FIG. 2, a cover 230 of the upper drawer unit 216 is in a closed configuration, blocking access to contents of the storage compartments 224, 226 thereof. A cover 232 of the lower drawer unit 218 is in an open configuration relative to the first storage compartment 224 thereof, where the cover 232 is clear of an opening 234 (e.g., open end, top) of the first storage compartment 224. As such, items stored in the first storage compartment 224 of the lower drawer unit 218 may be accessed (e.g., removed, added, replaced, used). However, items stored in the second storage compartment 226 of the lower drawer unit 218 are inaccessible as shown in FIG. 2, because the cover 232 is in a closed configuration relative to the second storage compartment 226 blocking access thereto.

According to an exemplary embodiment, the cabinet housing 212 includes a vertical arrangement of bays 250. Each bay 250 includes a rear portion 244 and a front portion 242. The front portion 242 of each bay 250 is configured to receive at least one drawer unit 216, 218 inserted through an opening and slid within the cabinet housing 212 toward the rear portion 244. Proximate to the rear portion 244 of each bay 250, the cabinet housing 212 includes a connector 248 (e.g., port, interface, link, coupling) for receiving a complementary connector 246 coupled each drawer unit 216, 218.

Coupling of the connectors 246, 248 allows for power and/or data communication between the controller 214 and the drawer units 216, 218, where the controller 214 is linked to the bays 250 of the cabinet housing 212 by wire 260. According to an exemplary embodiment, the connectors 246, 248 may be disconnected from each other when each drawer unit 216, 218 is slid away from the rear portion 244 of the bay 250, and may be reconnected when the respective drawer unit 216, 218 is then slid back to the rear portion 244 of the bay 250, reconnecting the connectors 246, 248.

According to an exemplary embodiment, at least one of the connectors 246, 248 includes one or more spring-loaded pins (see, e.g., pins 330 as shown in FIG. 3) and the other of the connectors 246, 248 includes one or more complementary ports configured to receive the pins. The pins may be pulled from the ports as the drawer units 216, 218 are slid away from the rear portion 244 of the cabinet housing 212, and then reconnected to the ports when the drawer units 216, 218 are slid back. In other contemplated embodiments, the controller 214 and each drawer unit 216, 218 remain in continuous communication (e.g., wired or wireless communication), even when the drawer units 216, 218 are slid partially out of each bay 250.

In various embodiments the controller 214 may include a broad range of control devices, such as a general purpose processor, application-specific integrated circuitry, a digital control interface mounted directly to the cabinet housing, a handheld remote control, a network of computers hard-wired to the cabinet system 210, or any other collection of circuitry components configured to conduct calculations or to facilitate the activities described herein. In contemplated embodiments, the controller 214 may be in wired or wireless communication, fiber optic communication, communication via mechanical linkage, or otherwise coupled to at least one of the cabinet housing 212 and/or one of the drawer units 216, 218 of the cabinet system 210. The controller 214 of FIG. 2 may also be linked to a network 254, such as an arrangement of hospital computers coupled to the internet or databases containing medical item information, medical personnel authorization information, or patient-related care information.

The controller 214 is configured to operate the locking mechanism 222 for each drawer unit 216, 218 via an actuator 252, such as an electric solenoid coupled to the locking mechanism 222. In various contemplated embodiments, the locking mechanism 222 includes at least one of a latch, a pin, a hook, a sliding bar, an interfering member, or another type of locking mechanisms, such as other remotely-controllable locking mechanisms that are commercially available. While the locking mechanism 222 in FIG. 2 is shown to selectively lock an underside 262 of each drawer unit 216, 218 to the rear portion 244 of each bay 250, it is contemplated that in other embodiments a locking mechanism may be configured to selectively lock any portion of each drawer unit 216, 218 to any other portion of the cabinet system 210.

The controller 214 is further configured to operate the covers 230, 232 of the drawer units 216, 218, such as to instruct one or more of the covers 230, 232 to move to an open configuration relative to one or more of the respective compartments 224, 226. According to an exemplary embodiment, movement of the covers 230, 232 may occur while each drawer unit 216, 218 is in one of the bays 250, such that the items of the drawer units 216, 218 may be then accessible when the drawer units 216, 218 are sufficiently slid out of the cabinet housing 212. In some embodiments, the covers 230, 232 are configured to move forward and backward (e.g., bi-directionally) relative to the compartments 224, 226.

Figure 5:
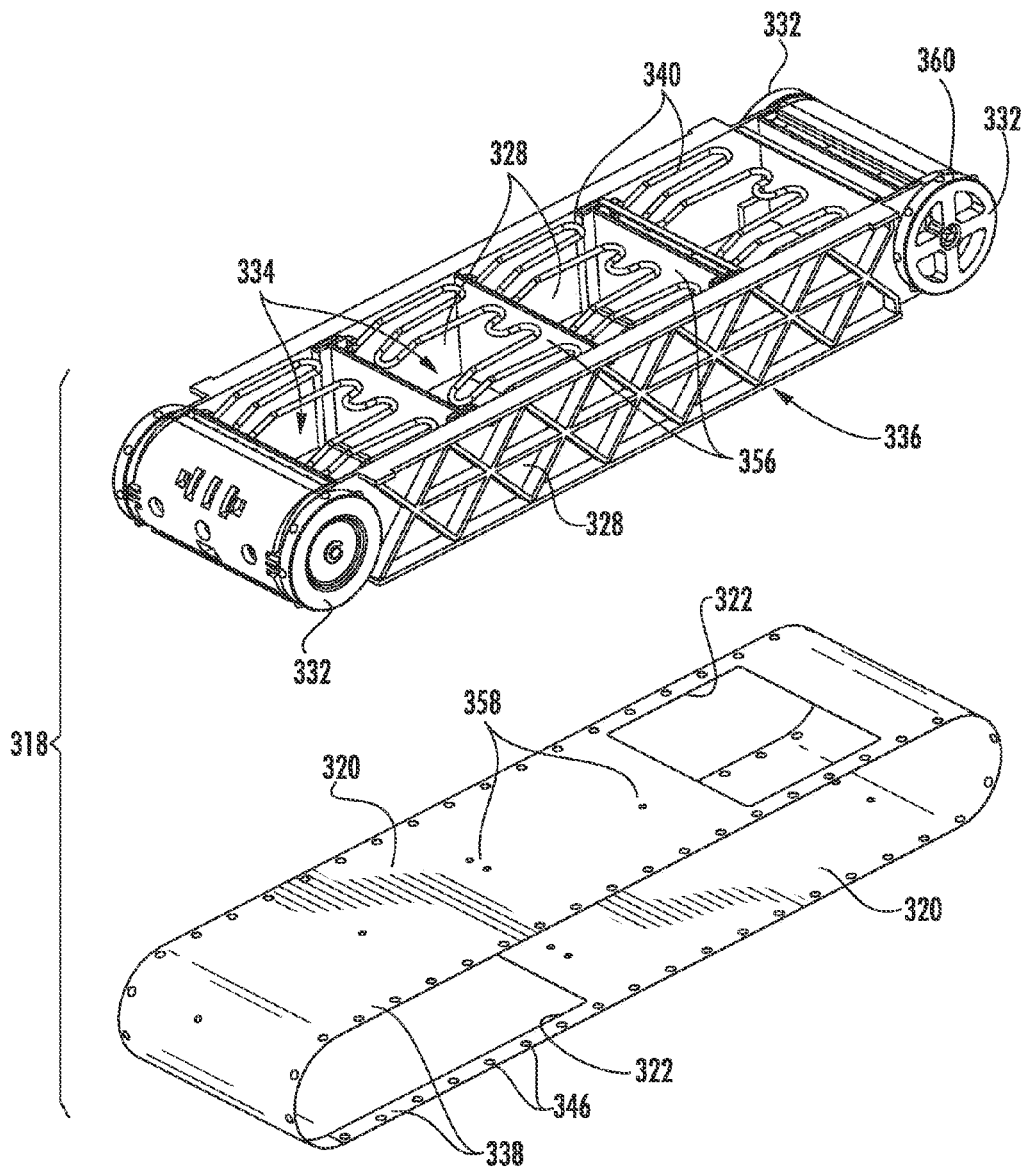
FIG. 5 is an exploded view of a portion of the drawer unit of FIG. 5.

The controller 214 is still further configured to operate a lock 256 coupled to each cover 230, 232. The lock 256 may be used to fix the respective cover 230, 232 in a particular configuration, orientation, or position when the corresponding drawer unit 216, 218 is slid away from the rear portion 244 of the cabinet housing 212. The lock 256 may include, but is not limited to a solenoid configured to engage locking holes in the covers 230, 232 (see, e.g., track 338 with perforations 346 as shown in FIG. 5), a spring-biased latch configured to engage each cover 230, 232 when the respective drawer unit 216, 218 is removed from the cabinet housing 212, and/or a high-ratio gear reduction (e.g., high-reduction gear box) of an electric motor 258 or other actuator used for controllably moving the covers 230, 232, where with the electric motor 258 stopped, the gear reduction is difficult to manually overcome. In still other embodiments the covers 230, 232 may be braked or locked by a motor brake or by reversing the polarity of the motor.

Still referring to FIG. 2, each drawer unit 216, 218 is coupled to an electronic memory 236 and a power source 238 for the electronic memory 236. Preferably, memory 236 and power source 238 are physically supported by their respective drawer units to move with the drawer units when they are moved. In various contemplated embodiments the electronic memory 236 may store data in a variety of states, such as volatile, non-volatile, random-access memory, read-only memory, solid states, and the like. The electronic memory 236 is configured to store (e.g., record, retain, hold) data associated with movement of the covers 230, 232. In some embodiments, the electronic memory 236 stores when the covers 230, 232 are directed to move by the controller 214, and/or when the covers 230, 232 are manually forced to move, such during an attempted theft of items stored in the cabinet system 210. In some embodiments, the electronic memory 236 stores such data regardless of whether the covers 230, 232 are fully moved to an open or closed configuration.

In some embodiments, the electronic memory 236 is coupled to a clock and stores the time, date, and duration of movements of the covers 230, 232 and/or relative configurations, positions, and orientations of the covers 230, 232 (e.g., data such as: 'compartment 226 of drawer unit 218 was open from 18:00:31 to 18:17:09 hours on Month, Day, Year). In other embodiments, the electronic memory 236 is configured to only store data when the covers 230, 232 have been manually forced to move, such as without authorization from the controller 214. Data directly associated with cover movement may include date representative of one or more signals generated by encoders (e.g., magnetic or optical) which monitor cover movement, cam switches, hall-effect sensors, capacitor discharge responsive to cover movement, sensor/switches state change in response to unauthorized cover movement, or monitoring of cover motor leads to detect movement of a belt-type cover. Upon reinsertion and connection of these drawers, the data or stated changes can be read and detected by the controller.

In variant contemplated embodiments, the power source 238 for the electronic memory 236 includes a battery, a power cell, a capacitor selectively charged by the controller 214, and/or other power sources, which may be coupled to each drawer unit 216, 218. Memory of events may be recorded on the electronic memory 236 and retained for download, even after the power source 238 has expired or terminated. In other embodiments, the electronic memory 236 may distinguish between authorized and unauthorized manual movements of the covers 230, 232. For example, the electronic memory may record when an authorized user is implementing a manual key override, such as during a power outage. In still other embodiments, an unauthorized movement of the covers 230, 232 may be detected by comparing the relative position of one of the covers 230, 232 before and after a drawer unit 216, 218 has been accessed, not requiring use of the electronic memory 236 and power source 238.

According to an exemplary embodiment, data may be transferred from the electronic memory 236 to the controller 214. When the drawer units 216, 218 are linked to the controller 214, data stored on the electronic memory 236 may be downloaded by the controller (e.g., processor) and analyzed. The data may include a broad spectrum of information, including by way of non-limiting example, a time and date of access or movement, contents of a drawer unit, a form of access (e.g., authorized or unauthorized, manual or automatic, etc.), accessing individual, form of authorization (e.g., prescription code, etc.), duration of access, and other such data. Analysis of the data may be designed to determine whether an attempt had been made to access to the items within the cabinet system 210 without authorization. While the electronic memory 236 is attached to each of the drawer units 216, 218 in FIG. 2, in other contemplated embodiments electronic memory may coupled to a controller, a cabinet housing, or elsewhere in a cabinet system, and analysis of data collected regarding movement of a cover for a drawer unit may be performed in real time, substantially as the cover is moved.

Figure 4:
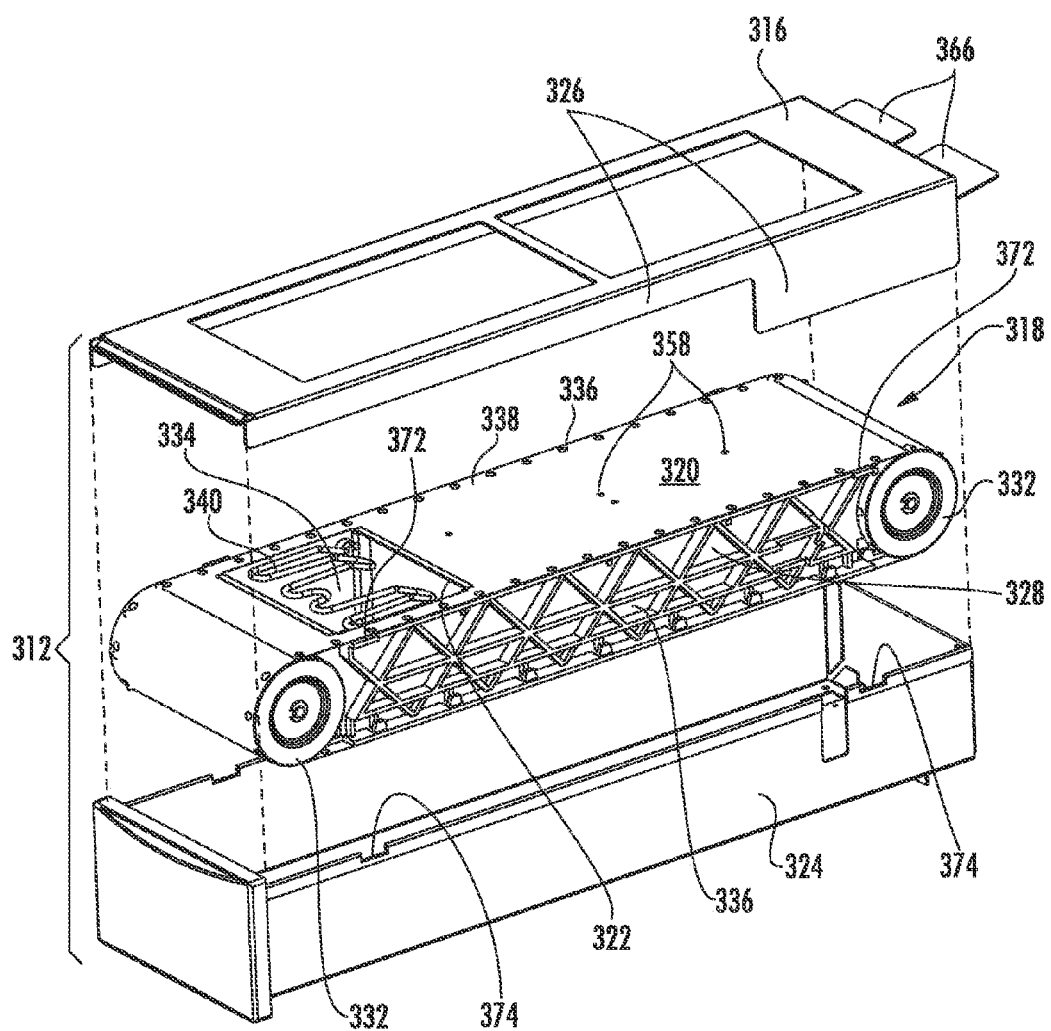
FIG. 4 is an exploded view of a drawer unit according to an exemplary embodiment of the invention.

Still referring to FIG. 2, at least one of the drawer units 216, 218 further includes a sensor 270 (e.g., photosensor, accelerometer, reed switch) coupled to the respective cover 230, 232. The sensor 270 is configured and arranged so as to directly or indirectly detect movement of the respective cover 230, 232, and to communicate the movement to the electronic memory 236 and/or to the controller 214. In some embodiments, the sensor 270 includes a potentiometer coupled to a pivot or wheel associated with movement of the cover (see, e.g., roller 332 as shown in FIG. 4). The potentiometer generates an electric signal responsive to movement of the cover 232 relative to the compartments 224, 226. In other contemplated embodiments, the cover 232 includes the electric motor 258 or other actuator configured to move the cover 232 in response to instructions from the controller 214. Manual movement of the electric motor 258 (e.g., reverse operation thereof) generates an electric signal that is directed to the electronic memory 236, which records data representative of the electric signal, and in turn of the manual movement of the cover 232.

According to an exemplary embodiment, each drawer unit 216, 218 includes an alarm 264. Another alarm 266 is coupled to the controller 214. In some embodiments, an electric signal generated in response to movement of one of the covers 230, 232 is also directed to at least one of the alarms 264, 266, which are configured to provide notice (e.g., alert, warn, broadcast) of unauthorized attempts to access items stored in the cabinet system 210. In some embodiments, the alarm 266 may be triggered subsequent to an unauthorized attempt, following analysis of data downloaded by the controller 214 from the electronic memory 236.

In various embodiments, the alarms 264, 266 may be a visual alarms, such as flashing lights, liquid crystal displays, light-emitting diode displays, warning messages, or other such visual signals. In other embodiments, the alarms 264, 266 may be audio alarms, such as beeping, sirens, pre-recorded messages, or other such audio signals, or a combination of both visual and audio signals. In some embodiments, the alarm 266 may be a silent alarm, not intended to be noticed by the someone triggering the alarm 266, such as an electronic-mail (e-mail) message automatically transmitted, which reports an incident to an email account of at least one pre-determined person (e.g., on-call doctor, hospital security, etc.).

Referring now to FIG. 3 an assembly 310 of drawer units 312 is attached to a rear portion 314 of a cabinet housing (see, e.g., cabinet housing 112 as shown in FIG. 1). The assembly 310 includes eight drawer units 312 in two rows, where each drawer unit 312 includes a cover 320 (e.g., sliding cover, indexing belt, hinged cover, removable cover, etc.) having an opening 322 therein. Each drawer unit 312 further includes side walls 328 (FIG. 4) that form compartments 334 interior to the drawer unit 312. Restraining bars 340 are biased to hold contents of the compartments 334 within the compartments 334 when the opening 322 of the cover 320 is aligned with each compartment 334. However, the bars 340 may be manually lifted or pivoted as necessary to remove items from the compartments 334. In still other embodiments, restraining bars are not included.

A visual interface, such as a light-emitting diode (LED) display 348, is coupled to a face 350 of at least one of the drawer units 312. The LED display 348 is configured to provide a visual signal to a user of the cabinet system. According to an exemplary embodiment, the visual signal of the LED display 348 indicates that unauthorized tampering has occurred with the respective drawer unit 312. In other embodiments, the LED display 348 provides other information, such as contents of the drawer unit 312, supply status information, etc.

When the drawer units 312 are stored within the cabinet housing, a controller (see, e.g., controller 214 as shown in FIG. 2) may be in electrical or other communication with the drawer units 312. However, the rear portion 314 of the cabinet housing may also include an interlock (e.g., a switch, spring pin connection, etc.) that can break communication between the controller and the drawer units 312 when a substantial portion of each drawer unit 312 is slid from the rear portion 314 of the cabinet housing (e.g., substantial enough that an unauthorized person could grip and pull the drawer unit 312 and/or cover 320 in order to force access to the compartments 334 thereof). As shown in FIG. 3, spring-loaded connection pins 330 separate connectivity between the drawer unit 312 from the rear portion 314, cutting communication between the drawer unit 312 and the controller, upon sliding of the drawer unit 312 from the rear portion 314 of the cabinet housing.

According to an exemplary embodiment, the cover 320 forms a closure with respect to the compartments 334 of the drawer unit 312. However, the cover 320 may be moved by an electric motor 352 (see FIG. 6), repositioning the opening 322 of the cover 320 to allow controlled access to one or more of the compartments 334 and/or to form a closure with respect to other compartments 334. In some embodiments, sliding of the drawer unit 312 from the rear portion 314 of the cabinet housing stops the flow of electricity to the electric motor 352 used to move the cover 320 interlocking the cover 320.

The rear portion 314 of the cabinet housing includes a circuitry board (e.g., firmware, programmable read-only memory (PROM)) and a releasable latch 354 (FIG. 7), both coupled to the controller. The latch 354 is configured to lock the drawer unit 312 to the rear portion 314 of the cabinet housing. An actuator 342 (e.g., solenoid, motorized pulley) may release the latch 354 when directed to do so by the controller. When unlocked, the drawer unit 312 may slide relative to the cabinet housing along a slide rail 344 that extends from the rear portion 314 of the cabinet housing.

Referring to FIG. 4 the drawer unit 312 includes a top frame 316 (e.g. cover), an insert 318, and a shell 324. The insert 318 fits within the shell 324, and the top frame 316, with flanges 326 extending therefrom, fits over the insert 318 and attaches to the shell 324. In some embodiments, the top frame 316 can be securely fastened to the shell 324 by means of a thumb screw or other fasteners, to prevent removal of the insert 318 from the shell 324.

The insert 318 includes the cover 320, a side wall 328, and rollers 332. The cover 320 may slide relative to the side wall 328 and compartments 334 via the rollers 332. In some embodiments, the insert 318 includes intermediary flanges 372 extending from the side wall 328 (or from the shell 324) to contact receiving portions 374 of the shell 324 in order to separate the cover 320 from the shell 324 during movement of the cover 320 (i.e., providing space for the cover 320 to move).

Referring now to FIG. 5, the insert 318 includes the cover 320 and a body 336. The body 336 includes divider walls 356 and side walls 328, which together form compartments 334. According to an exemplary embodiment, some of the divider walls 356 may be fixed while others may be removable, providing adjustable compartmentalization. In some embodiments, the insert 318 can optionally have two, three, or four compartments 334, depending upon the use of the removable divider walls 356. Items of varying sizes may be stored in differently sized compartments 334. In such embodiments, the cover 320 may include two openings 322, one configured to match a larger compartment and the other sized for a smaller compartment. Depending upon the use, there may be more than 2 opening sizes. The fixed divider walls 356 may be injection molded with the body 336, glued, welded, or otherwise fixed to the body 336. In other embodiments, a body of an insert may be both longer and/or deeper (or shorter and/or narrower) than the body 336 of FIG. 5. In some such embodiments, a body of an insert may include up to six compartments, with ten such inserts in a drawer assembly (cf. assembly 310 as shown in FIG. 3).

According to an exemplary embodiment, the cover 320 may be an indexing belt made of a continuous material, such as about 0.005 inch thick stainless steel sheet. Other contemplated embodiments include belts of thicker clear mylar, polycarbonate sheet, rubber, or other materials. The cover 320 is preferably made to be flexible, such that the cover 320 may bend about a portion of the insert 318, such as a roller 332. Bending of the cover 320 allows for a more-compact drawer unit design, because unused portions of the cover 320 may be folded about the body 336. Other contemplated embodiments include flexible covers that are not belts, such as straps, strips, bands, and the like, which may not slide fully around the body 336. For example, some embodiments include spools for winding the flexible covers for storage and control thereof.

Still referring to FIG. 5, the cover 320 is designed with a series of small holes 358 that are in coded sequences, readable by a sensor. The coded sequences vary at different positions on the cover 320, such that detection of a portion of the coded sequence by the sensor provides positional information to the controller of the cover 320 orientation relative to the body 336. Still other embodiments count rotations of one of the rollers 332 to determine the position of the cover 320 relative to a starting position thereof. In some embodiments, holes may be noncircular, such as diamond-shaped, teardrop shaped, or otherwise shaped. Including a corner (e.g., crack initiation location, vertex) to the shape of the holes may improve tamper evidence by facilitating a controlled tearing of the cover if unauthorized, forced entry is attempted.

The rollers 332 are positioned on the longitudinal ends of the insert 318, where at least one of the rollers 332 is in the form of a sprocket 360 (with teeth). In such embodiments, the cover 320 includes perforated tracks 338. The teeth of the sprocket 360 fit the perforations 336, such that the cover 320 is moved relative to the body 336 via controlled rotation of the sprocket 360. In other embodiments, rollers 332 have a high-friction surface, such as sandpaper grit or a gripping rubber, for providing force to move the cover 320, without teeth. The rollers 332 may be injection molded from Celcon or Delrin materials, cast or molded metals, and/or composites.

Figure 6:
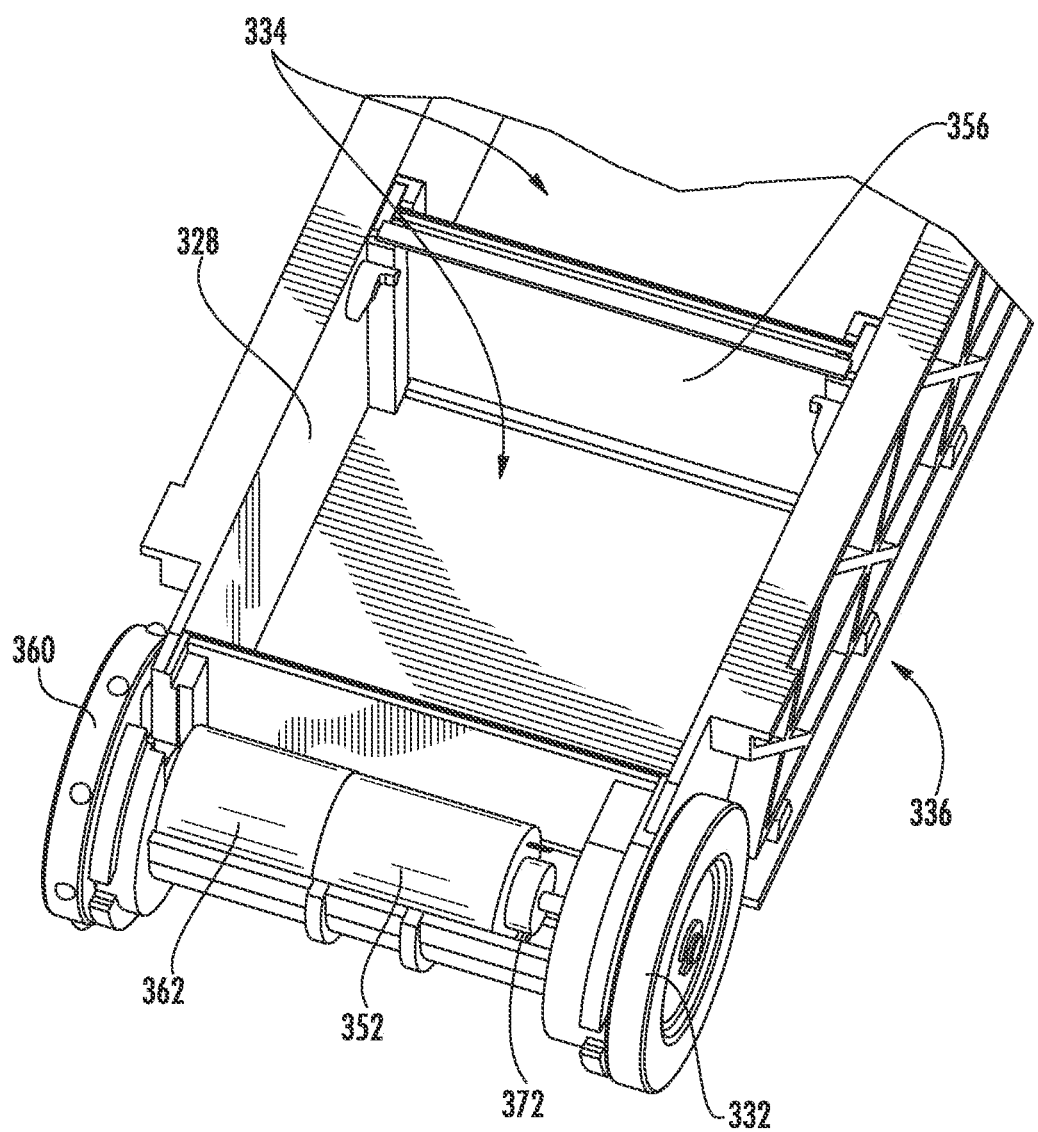
FIG. 6 is a perspective view of a portion of the drawer unit of FIG. 5.

Referring to FIG. 6 the insert 318 of the drawer unit 312 includes the side walls 328, the divider wall 356, the rollers 332 (one being a sprocket 360), the electric motor 352, and a gear reduction 362. The electric motor 352 (e.g., direct current motor) is coupled to the gear reduction 362, which in turn is coupled to the sprocket 360, coupled to the cover 320. According to an exemplary embodiment, the electric motor 352 is selectively powered by the controller via a power/data bus coupled to the insert 318, and selectively connected to a power source when the drawer unit 312 is locked within the cabinet housing.

The insert 318 of FIG. 5 may additionally include a data storage device 272 (FIG. 6) coupled to the power/data base. In some embodiments, the data storage device is coupled to the electric motor 352. Manual sliding of the cover 320 forces the electric motor 352 to operate in reverse, generating an electric signal that is transmitted on the power/data bus. Data representative of the electric signal is stored on the data storage device 272. In other embodiments, the data storage device 272 is a mechanical detection device, such as a spring-loaded interlock. Manual sliding of the cover 320 triggers the interlock, which locks the cover and may additionally trigger an alarm.

Figure 7:
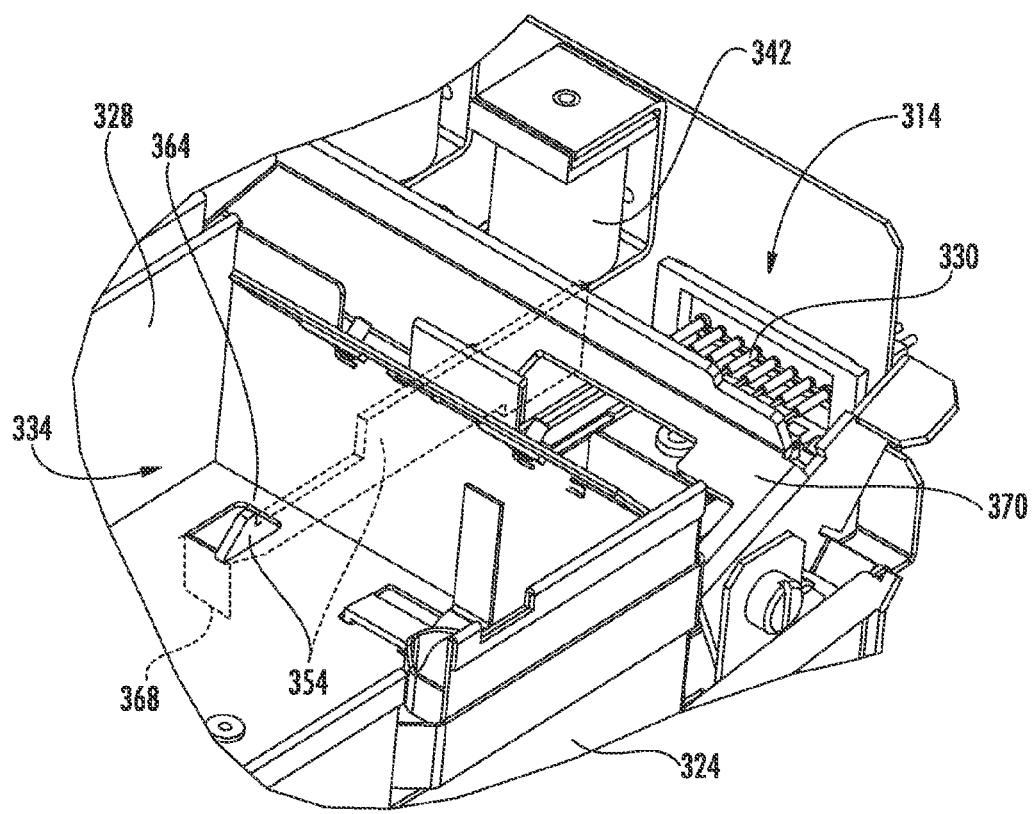
FIG. 7. is a perspective view of a portion of the cabinet system of FIG. 3.

Referring now to FIG. 7, the shell 324 may be locked to the rear portion 314 of the cabinet housing by a latch 354. The latch 354 extends beneath the shell 324 and connects to the shell 324 via a strike 364 (e.g., reinforced hole, catch) coupled to the shell 324. The latch 354 is coupled the actuator 342, which may be directed by the controller to release the shell 324. A security deflection tab 366 (e.g., "fishability bracket"), as shown in FIG. 4, may serve to block attempts to manipulate the latch 354 from an above position, such as by drilling a hole in the top of the cabinet housing and reaching down through the hole with a rod to release the latch 354. A second tab 368 extends from the shell 324 to block attempts to manipulate the latch 354 from the front of the cabinet housing. A manual release plate 370 allows for release of the drawer units 312 by key, code, etc., during a power outage (e.g., manual key override).

The construction and arrangements of cabinet system, as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention

What is claimed is:

1. A medical item storage cabinet system, comprising:
a cabinet including a drawer bay and a locking mechanism;
a drawer located within the drawer bay of the cabinet, the drawer slidable relative to the drawer bay between an open position in which the drawer extends out of the drawer bay and a closed position in which the drawer is located within the drawer bay, the locking mechanism configured to engage the drawer in the closed position, the drawer including:
a first compartment;
a second compartment;
a cover movable by an electric motor to a first position to permit access to the first compartment and limit access to the second compartment and moveable to a second position to permit access to the second compartment and limit access to the first compartment;

an electronic memory coupled to the drawer configured to store information representative of movement of the cover that occurs when the drawer is in the open position;

a power source coupled to the drawer configured to supply power to the electronic memory;

wherein the electronic memory and the power source are physically supported by the drawer such that the electronic memory and the power source move with the drawer relative to the drawer bay.

2. The system of claim 1, further comprising a controller located within the cabinet and a connector coupled to the electronic memory and physically supported by the drawer, wherein the connector is electrically coupled to the controller when the drawer is in the closed position and decoupled from the controller when the drawer is in the open position, and further wherein the controller is configured to receive the information representative of movement of the cover that occurs when the drawer is in the open position from the electronic memory when the connector is coupled to the controller.

3. The system of claim 1, wherein the power source is one of a rechargeable battery or a capacitor.

4. The system of claim 3, wherein the cover is a continuous belt including a first opening sized to permit access to the first compartment and a second opening sized to permit access to the second compartment.

5. The system of claim 1, wherein the information representative of movement of the cover stored by the electronic memory includes time, date and cover movement duration information.

6. The system of claim 5, further comprising a sensor configured to detect the movement of the cover, the sensor coupled to the electronic memory and configured to provide the information representative of movement of the cover to the electronic memory.

7. The system of claim 1, further comprising a display device coupled to a face of the drawer, the display device configured to display a visual indication that movement of the cover occurred while the drawer was in the open position.

8. A cabinet system for securely storing items, comprising:
a cabinet housing having a locking mechanism;
a controller associated with the cabinet housing and configured to operate the locking mechanism; and
a drawer unit configured to be releasably locked at least partially within the cabinet housing by the locking mechanism, and slidable within a portion of the cabinet housing when released by the locking mechanism, the drawer unit comprising:
at least one storage compartment configured to store at least one item;
a cover movable to an open configuration and a closed configuration, wherein the cover limits access to the at least one item of the storage compartment when the cover is in the closed configuration;
a sensor configured to detect the movement of the cover;
an electronic memory physically supported by the drawer unit such that the electronic memory moves with the drawer unit relative to the cabinet housing, the electronic memory coupled to the sensor and configured to store data associated with a movement of the cover detected by the sensor;
a connector coupled to the electronic memory and physically supported by the drawer unit, wherein the connector electrically couples to the controller when the drawer unit is received within the cabinet housing, wherein the connector decouples from the controller when the drawer unit extends out of the cabinet housing, and further wherein the controller is configured to receive the data from the electronic memory when the connector is coupled to the controller.

9. The cabinet system of claim 8, further comprising a power source physically supported by the drawer unit such that the power source moves with the drawer unit relative to the cabinet housing, the power source coupled to and supplying power to the electronic memory.

10. The cabinet system of claim 9, wherein the power source is one of a rechargeable battery or a capacitor.

11. The cabinet system of claim 8, wherein the controller is located within the cabinet housing.

12. The cabinet system of claim 8, wherein the electronic memory stores time and date information associated the cover movement data.

13. The cabinet system of claim 8, further comprising an LED coupled to a front face of the drawer unit, the LED configured to display a visual indication that movement of the cover was detected by the sensor.

14. The cabinet system of claim 8, wherein the drawer unit further comprises an electric motor coupled to the controller and configured to move the cover relative to the at least one storage compartment when directed to do so by the controller.

15. The cabinet system of claim 14, wherein the electronic memory is configured to store data associated with the movement of the cover when the movement occurs without being driven by the electric motor.

16. The cabinet system of claim 14, wherein the electronic memory is configured to store data associated with the movement of the cover only when the movement occurs without being driven by the electric motor.

17. The cabinet system of claim 14, wherein the electric motor is the sensor and is configured to generate a signal when driven by a manual movement of the cover, and wherein the electronic memory is configured to receive the signal and to store data representative of the signal.

18. A cabinet system for securely storing medical items, comprising:
a cabinet housing;
a drawer moveable relative to the cabinet housing between an open position in which the drawer extends out of the cabinet housing and a closed position in which the drawer is located within the cabinet housing, the drawer comprising:
a plurality of storage compartments;
a cover moveable relative to the plurality of storage compartments to provide access to each of the plurality of storage compartments;
a sensor configured to detect manually forced movement of the cover;
an electronic memory physically supported by the drawer such that the electronic memory moves with the drawer relative to the cabinet housing, the electronic memory coupled to the sensor and configured to store data associated with a manually forced movement of the cover detected by the sensor; and
an indicator display coupled to a front face of the drawer, the indicator display configured to display a visual indication that manual forced movement of the cover was detected by the sensor;
a locking mechanism configured to lock the drawer when the drawer is in the closed position; and
a controller associated with the cabinet housing and configured to operate the locking mechanism.

19. The cabinet system of claim 18, further comprising a controller and an electric motor configured to slide the cover relative to the storage compartments when directed to do so by the controller.

20. The cabinet system of claim 19, wherein the electronic memory stores time and date information associated the with the data of a manually forced movement of the cover detected by the sensor.

\* \* \* \* \*